United States Patent
Ballam et al.

(10) Patent No.: US 11,033,694 B2
(45) Date of Patent: Jun. 15, 2021

(54) INHALER WITH ORIENTATION SENSOR

(71) Applicant: PHILIPS HEALTHCARE INFORMATICS, INC., Cambridge, MA (US)

(72) Inventors: Robert Scott Ballam, Eatons Hill (AU); Robert Bruce Ganton, San Diego, CA (US)

(73) Assignee: Koninklijke Philips N.V., Eindhoven (NL)

( * ) Notice: Subject to any disclaimer, the term of this patent is extended or adjusted under 35 U.S.C. 154(b) by 1070 days.

(21) Appl. No.: 14/798,560

(22) Filed: Jul. 14, 2015

(65) Prior Publication Data

US 2016/0082208 A1 Mar. 24, 2016

Related U.S. Application Data

(60) Provisional application No. 62/103,954, filed on Jan. 15, 2015, provisional application No. 62/053,703, filed on Sep. 22, 2014.

(51) Int. Cl.
*A61M 15/00* (2006.01)
*A61M 16/00* (2006.01)

(52) U.S. Cl.
CPC ...... *A61M 15/009* (2013.01); *A61M 15/0065* (2013.01); *A61M 16/0003* (2014.02);
(Continued)

(58) Field of Classification Search
CPC ........ A61M 11/00; A61M 11/001–008; A61M 11/02–08; A61M 13/00;
(Continued)

(56) References Cited

U.S. PATENT DOCUMENTS 5,284,133 A * 2/1994 Burns .................. A61M 15/009
128/200.14
6,202,642 B1 3/2001 McKinnon et al.
(Continued)

FOREIGN PATENT DOCUMENTS

WO 2014004437 A1 1/2014
WO 2014068504 A2 5/2014
(Continued)

OTHER PUBLICATIONS

International Search Report and Written Opinion—PCT/US2015/040467—ISA/EPO—dated Sep. 24, 2015.

*Primary Examiner* — Samchuan C Yao
*Assistant Examiner* — Ned T Heffner
(74) *Attorney, Agent, or Firm* — Michael W. Haas

(57) ABSTRACT

Various embodiments include an inhaler for oral delivery of medication that includes an actuation detector configured to provide an actuation signal in response to release of the medication from the inhaler, and an accelerometer configured to measure an orientation of the inhaler. The inhaler may include a processor, coupled to the actuation detector and the accelerometer, configured with processor-executable instructions to perform operations to determine a quality of use of the inhaler based on the actuation signal provided by the actuation detector and the orientation of the inhaler measured by the accelerometer.

8 Claims, 4 Drawing Sheets

(52) U.S. Cl.
CPC ..... *A61M 16/024* (2017.08); *A61M 2205/215* (2013.01); *A61M 2205/276* (2013.01); *A61M 2205/3576* (2013.01); *A61M 2205/3592* (2013.01); *A61M 2205/50* (2013.01)

(58) Field of Classification Search
CPC .... A61M 15/00–0011; A61M 15/0028; A61M 15/0065–0078; A61M 15/0085; A61M 15/009; A61M 15/0091; A61M 15/0093; A61M 15/06; A61M 15/08; A61M 15/085
See application file for complete search history.

(56) References Cited

U.S. PATENT DOCUMENTS

| | | | |
|---|---|---|---|
| 8,807,131 B1* | 8/2014 | Tunnell | A61M 16/0051 128/200.23 |
| 2004/0163641 A1* | 8/2004 | Tyvoll | A61M 15/025 128/200.23 |
| 2005/0161467 A1 | 7/2005 | Jones | |
| 2009/0107492 A1* | 4/2009 | Ooida | A61M 11/005 128/200.21 |
| 2013/0008436 A1 | 1/2013 | Von Hollen et al. | |
| 2013/0269685 A1 | 10/2013 | Wachtel et al. | |

FOREIGN PATENT DOCUMENTS

| | | |
|---|---|---|
| WO | 2014204511 A2 | 12/2014 |
| WO | 2015006701 A2 | 1/2015 |

\* cited by examiner

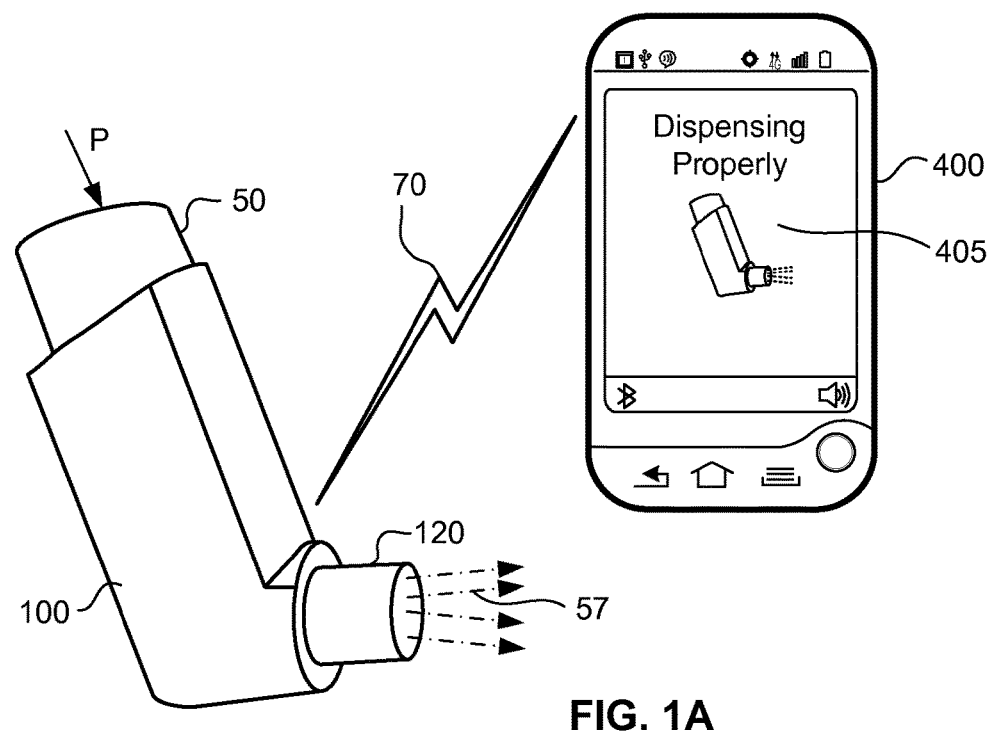
FIG. 1A
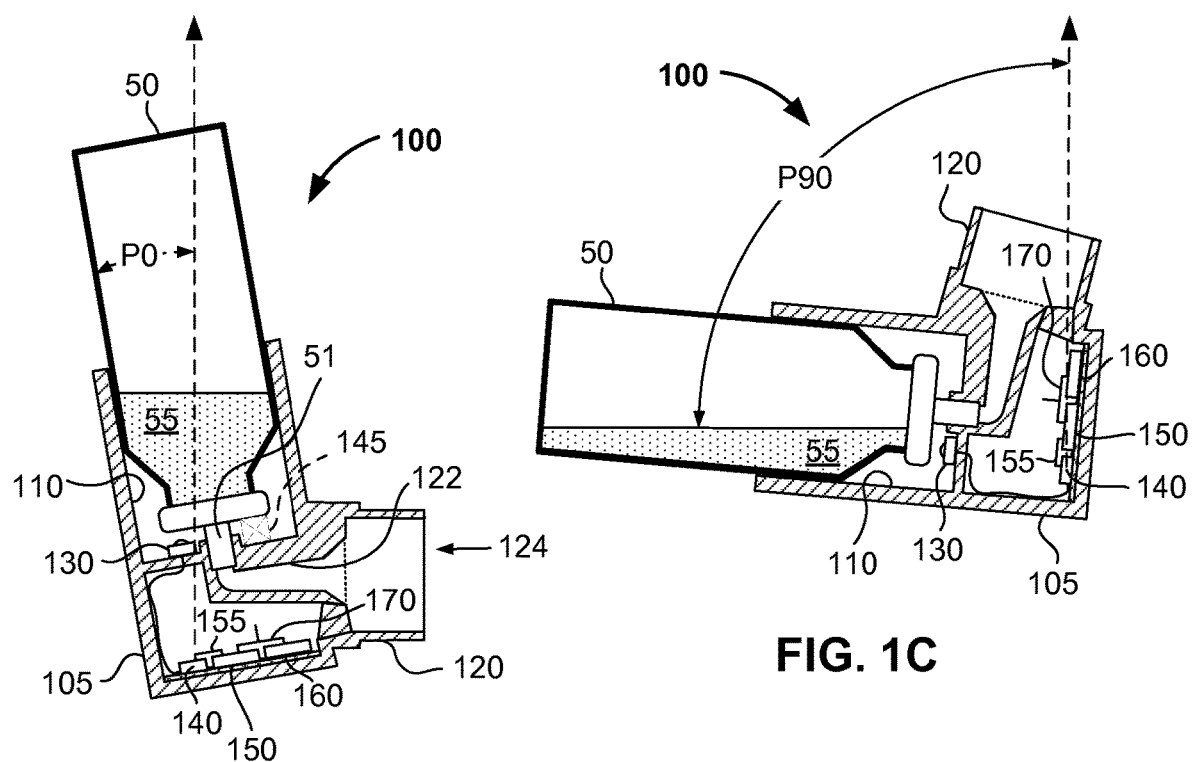
FIG. 1B
FIG. 1C

INHALER WITH ORIENTATION SENSOR

RELATED APPLICATIONS

This application claims the benefit of priority to U.S. Provisional Patent Application 62/053,703, entitled "Inhaler with Orientation Sensor," filed Sep. 22, 2014, and U.S. Provisional Patent Application 62/103,954, entitled "Inhaler with Orientation Sensor," filed Jan. 15, 2015, the entire contents of both of which are hereby incorporated by reference for all purposes.

BACKGROUND

Medical practitioners often find it useful to monitor patient compliance to a prescribed schedule of taking medications outside of the doctor's office or other medical facility. Information regarding patient compliance to a prescribed schedule is particularly useful for patients using medications dispensed using an inhaler. An inhaler is a dispensing device used for delivering medication into a user's body via that user's lungs.

SUMMARY

The systems, methods, and devices of the various embodiments provide an inhaler for oral delivery of medication to a user's lungs that includes an actuation detector, an accelerometer, and a processor coupled to both the actuation detector and the accelerometer. The inhaler includes a main body with a medication reservoir and a mouthpiece. The medication reservoir is configured to hold the medication, which may be contained in a medication canister. The mouthpiece includes an aperture configured to deliver the medication from the medication reservoir. The actuation detector is configured to provide an actuation signal in response to release of the medication from the inhaler. The actuator detector may be configured to provide the actuation signal throughout the entire release of medication (not just upon initial actuation), thereby providing a duration that the medication was dispensed. The accelerometer is configured to measure accelerations, including the gravity gradient that may be used by the processor to determine an orientation of the main body. The processor is configured with processor-executable instructions to perform operations using an actuation signal from the actuation detector and the orientation from the accelerometer to determine a quantity and/or quality of use of the inhaler.

In various embodiments, determining the quality of use of the inhaler may include discounting an activation duration by an improper usage duration. The activation duration may be based on a total period in which the medication is released. The improper usage duration may be based on a period during the activation duration in which the measured orientation of the inhaler deviates from a preferred orientation by an amount that exceeds a predetermined proper orientation threshold.

In various embodiments, the inhaler may include an inhibitor that may be configured to prevent the inhaler from dispensing the medication. The processor may be further configured with processor-executable instructions to activate the inhibitor based on the quality of use of the inhaler determined.

In various embodiments, the processor may be further configured with processor-executable instructions to determine whether the inhaler has been agitated a predetermined amount (e.g., sufficient to ensure the medication is properly mixed for dispensing). The quality of use may reflect the improper agitation in response to determining that the inhaler has not been agitated the predetermined amount. In addition, the processor may be further configured with processor-executable instructions to determine whether the orientation of the inhaler departs from a preferred orientation (e.g., an angle away from the preferred orientation) by an amount that exceeds a predetermined proper orientation threshold. In this way, the quality of use may reflect an improper orientation in response to determining that the orientation of the inhaler departs from the preferred orientation by the amount that exceeds the predetermined proper orientation threshold.

In various embodiments, a wireless signal transmitter may be coupled to the processor. The wireless signal transmitter may be configured to transmit data to a computing device remote from the inhaler to enable the computing device to determine the quality of use of the inhaler. In addition, the inhaler may include an indicator configured to alert a user regarding the quality of use. The processor may be configured with processor-executable instructions to activate the indicator based on the quality of use of the inhaler determined. A memory coupled to the processor may be configured to store data indicating the quality of use of the inhaler. The accelerometer may be configured to measure accelerations associated with movement of the inhaler. In this way, the processor may be configured with processor-executable instructions to cause the wireless signal transmitter to transmit a data signal indicating the accelerations measured by the accelerometer to the computing device. The computing device may be configured to analyze data provided in the data signal to infer contextual information corresponding to user activities before or after activation of the inhaler.

In various embodiments, a method of oral delivery of a medication to a user's lungs with an inhaler includes receiving an actuation signal in response to release of the medication from the inhaler. A first accelerometer measurement may be received indicating an orientation of the inhaler. The actuation signal and the first accelerometer measurement may be stored in a memory. In addition, a determination may be made as to whether the orientation of the inhaler exceeds a predetermined proper orientation threshold. In this way, a quality of use of the inhaler may be determined based on the actuation signal and the first accelerometer measurement.

In various embodiments, an activation duration may be determined based on a total period in which the medication is released. In addition, an improper usage duration may be determined based on a period during the activation duration in which the orientation of the inhaler deviates from a preferred orientation by an amount that exceeds the predetermined proper orientation threshold. In this way, a discount of the improper usage duration may be applied to the activation duration for determining the quality of use of the inhaler.

In various embodiments, a properly dispensed dosage of the medication may be indicated in response to determining that the orientation of the inhaler does not exceed the predetermined proper orientation threshold. In addition, accelerometer data may be monitored to determine an amount of agitation imparted to the medication, and a determination may be made regarding whether the amount of agitation meets an acceptable minimum for dispensing the medication in response to receiving the actuation signal. An inhibitor configured to prevent the inhaler from dispensing the medication may be activated, preventing dispensing of medication based on the quality of use. For example, in response to determining that the amount of agitation imparted to the medication does not meet the acceptable minimum for dispensing the medication, the inhibitor may be activated. A second accelerometer measurement indicating movement information of the inhaler may be received, and the movement information may be used to determine contextual information associated with a predetermined type of activity by a user of the inhaler. The movement information may be stored in response to determining the movement information is the contextual information. In addition, the movement information may be transmitted in response to determining the movement information is the contextual information. A time-of-day associated with the actuation signal of a properly and/or improperly dispensed dosage may be stored in a memory. In addition, a count of a plurality of such actuation signals may be maintained in response to activation of the medication release mechanism.

Further embodiments include a method of performing the various operations performed by the inhaler described above.

Further embodiments include a computing device having means for performing functions corresponding to the method operations described above.

Further embodiments include a non-transitory processor-readable storage medium having stored thereon processor-executable instructions configured to cause a processor to perform various operations corresponding to the above-discussed method operations.

BRIEF DESCRIPTION OF THE DRAWINGS

The accompanying drawings, which are incorporated herein and constitute part of this specification, illustrate exemplary aspects of the invention, and together with the general description given above and the detailed description given below, serve to explain the features of the invention.

FIG. 1A is a schematic diagram of an inhaler communicating with a computing device suitable for use with the various embodiments.

FIG. 1B is a cross-sectional side view illustrating an exemplary inhaler oriented in an optimal orientation angle according to various embodiments.

FIG. 1C is a cross-sectional side view illustrating an exemplary inhaler oriented in an undesirable orientation angle according to various embodiments.

DETAILED DESCRIPTION

Figure 2:
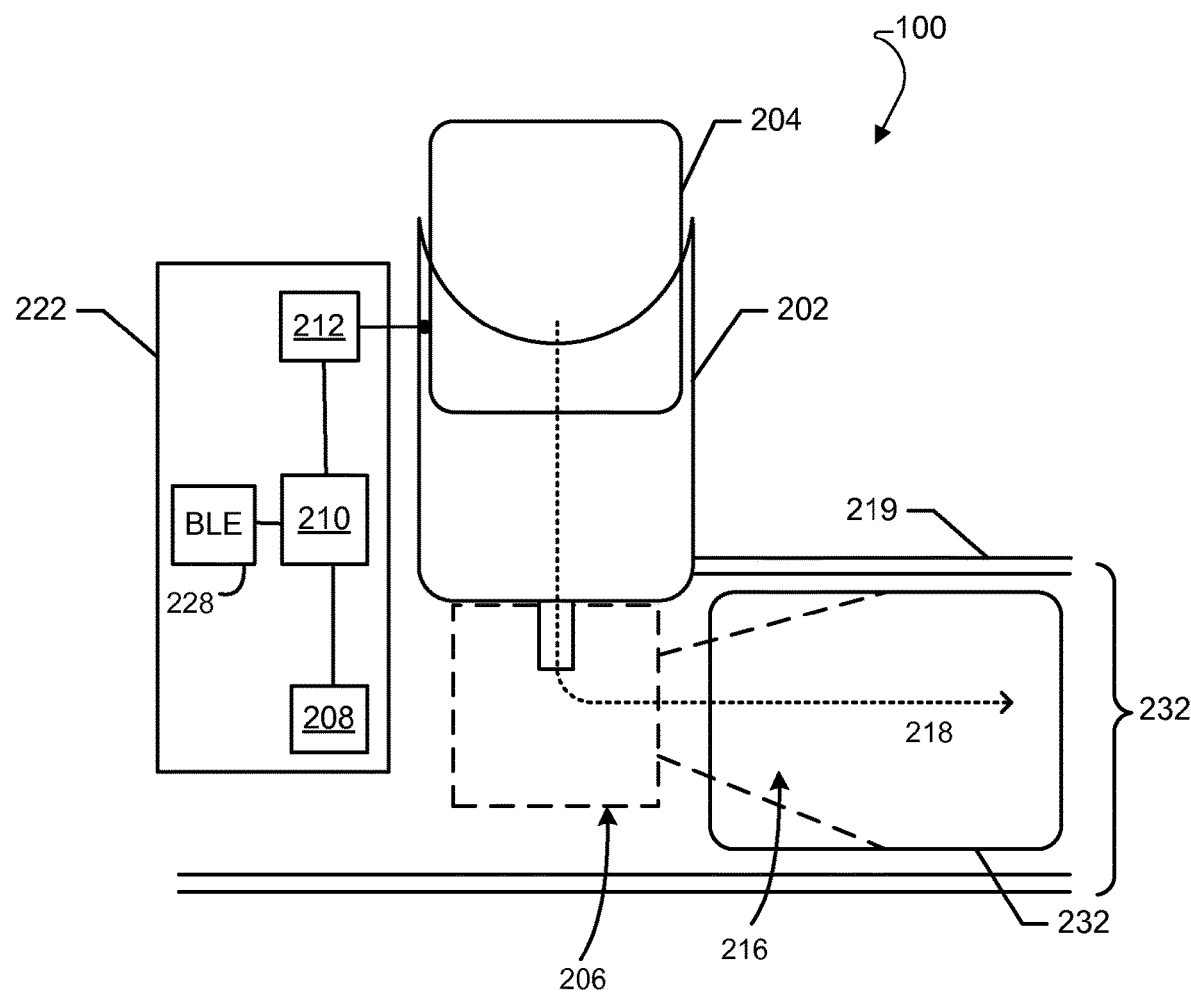
FIG. 2 is a component block diagram of an exemplary inhaler according to various embodiments.

The various aspects will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The term "inhaler" is used herein to refer to a medical device used for delivering medication into a body via the lungs. An inhaler includes a medication reservoir and a mouthpiece. The medication reservoir may hold the medication directly or hold a medication canister. The medication canister may be a replaceable component used to supply or replenish a supply of medication for use with the inhaler.

Modern inhalers may include a microprocessor and radio transmitter for monitoring and reporting each time the inhaler is used. The microprocessor may be configured to receive an input, each time the inhaler is pumped, for reporting patient usage of the inhaler. While such systems measure compliance with a schedule of usage, they fail to monitor whether the inhaler was properly oriented when used, which may mean a proper dosage was not administered. For example, when an inhaler is held horizontally, it may not administer the correct dosage or may not last as long as specified. The patient may be unaware or forget that an improperly oriented device does not dispense properly. In addition, the prescribing medical practitioner may not learn of the incorrect usage.

The term "accelerometer" as used herein refers to a device that measures physical acceleration experienced by the device, which may be used to determine a measured orientation, movement direction, and/or position of the device. The measured orientation, movement direction, and/or position may be relative to a reference direction, such as a vertical direction.

The term "wireless signal transmitter" as used herein refers to an electronic device that produces radio waves with the aid of an antenna. The transmitter itself generates a radio frequency alternating current, which is applied to the antenna. When excited by this alternating current, the antenna radiates radio waves that may carry signals for communications with a computing device configured to receive and decipher the signals carried by the radio waves.

The term "computing device" is used herein to refer to any one or all of laptop computers, desktop computers, servers, tablet computers, smart books, palm-top computers, cellular telephones, smart phones, personal or mobile multimedia players, personal data assistants (PDA's), wireless electronic mail receivers, Internet enabled cellular telephones, Wi-Fi enabled electronic devices, and similar electronic devices that include a processor and configured to communicate with an inhaler in accordance with various embodiments.

The various embodiments enable the monitoring and/or reporting of a quantity and/or quality of use of an inhaler based on various measurements. A measurement may come from an actuation detector configured to detect and/or provide an actuation signal in response to release of medication from the inhaler. An accelerometer may also be included in the inhaler to measure an orientation thereof. Modern accelerometers are energy efficient, inexpensive, and small enough to fit inside an inhaler, along with other electronic components. An accelerometer in an inhaler may be used to track the orientation of the inhaler before, during, and after release of the medication from the inhaler. In addition, by including a wireless signal transmitter, such as a Bluetooth®, Bluetooth low energy (BLE), or Wi-Fi transceiver, the orientation of the inhaler during use may be reported to a medical practitioner or other authorized entity by way of a computing device configured to receive the orientation information. The orientation information of the inhaler during use may be monitored remotely at a medical practitioner's office and corrective measures may be taken, if necessary. For example, if the inhaler is held too far from vertical when used, the correct amount of medication may not be dispensed. Using an accelerometer to detect and report an improper orientation angle when the inhaler is being used may provide a medical practitioner with needed information as to why a particular medication has not been as effective as expected (i.e., by tilting the inhaler too much, the patient is not administering the medication properly).

FIG. 1A illustrates an embodiment inhaler 100 communicating with a computing device 400 remote from the inhaler 100. The inhaler 100 includes a medication canister 50 held in a medication reservoir (see, 110 in FIG. 1B) of the inhaler 100. The medication canister 50 may be pressed, with a force P, down into the medication reservoir to release medication contained within the medication canister 50. The released medication may be expelled from the mouthpiece 120 as a dispensed medication dosage 57 for oral delivery to a user's lungs of a user to whom it is administered. In order to ensure that the dispensed medication dosage 57 is of a sufficient amount, the inhaler 100 may include an actuation detector configured to detect when the inhaler is being used to dispense medication and/or an accelerometer configured to measure the orientation of the inhaler 100. In this way, in addition to tracking when a user is using the inhaler 100, the actuation detector and/or the accelerometer may be used to determine a duration and quality of use of the inhaler 100. For example, the actuation detector may provide an actuation signal to a processor for determining the entire duration that the inhaler 100 is actuated, and the processor may monitor data from the accelerometer throughout the duration of actuation to determine the orientation of the inhaler at all times that medication was being dispensed, and not just at the instant the user actuates the inhaler 100.

An internal processor of the inhaler 100 may be coupled to the actuation detector and the accelerometer. In this way, the processor may correlate a detected actuation of the inhaler 100 with a measured acceleration and/or orientation of the inhaler 100. In addition, the processor may map the correlation of various accelerations/orientations events to use of the inhaler 100. A wireless signal transmitter coupled to the processor may be used to transmit data 70 to the computing device 400. In addition to reporting when the inhaler 100 has dispensed medication, the measured orientation may be reported and used to determine whether the measured orientation is likely to dispense the sufficient amount of the medication. Thus, in response to receiving the data 70, the computing device 400 may receive orientation information indicating whether the user oriented the inhaler 100 properly when pressing the medication canister 50. The computing device 400 may store the received orientation information locally, display the received orientation information locally (e.g., see the display 405 of the computing device in FIG. 1A), and/or transmit that orientation information to a medical practitioner or other authorized entity by way of a network.

In some embodiments, the inhaler 100 may include an inhibitor configured to prevent the inhaler 100 from dispensing the medication based on a quality of use determination. For example, the processor may signal the inhibitor to prevent dispensing of medication when the measured orientation of the inhaler (based on data from the accelerometer) deviates from a preferred orientation by a measure that exceeds a predetermined proper orientation threshold. In this manner, when the inhaler 100 is being held at an improper angle such that the inhaler 100 may not fully dispense a medication dosage 57, the inhibitor may prevent an improper dosage from being dispensed.

FIGS. 1B and 1C illustrate cross-sectional side views of the inhaler 100 in two different orientations. FIG. 1B shows the inhaler 100 oriented at an optimal orientation angle P0, while FIG. 1C shows the inhaler 100 rotated counter-clockwise at a ninety degree orientation angle P90, which is not desirable (i.e., undesirable). The optimal orientation angle P0 may have the medication canister 50 slightly tilted away from vertical. This allows the last of the medication 55 to pool to one side inside the medication canister 50 and may maximize the amount of medication 55 that can be extracted. While the optimal orientation angle P0 is a desirable orientation angle for using the inhaler 100, it is not the only orientation angle at which the inhaler is likely to function properly. Thus, a range of orientation angles deviating in either direction from the optimal orientation angle P0 may be predetermined to be proper for dispensing the medication 55. In this way, any orientation angle outside the range of orientation angles predetermined to be proper for dispensing the medication 55 may be referred to as exceeding a predetermined proper orientation threshold. When the inhaler 100 is held at an angle that exceeds the predetermined proper orientation threshold, the inhaler 100 is tilted too far to be effective. For example, any measured orientation angle greater than forty-five (45) degrees from the optimal orientation angle P0 may be determined to exceed the predetermined proper orientation threshold.

FIG. 1B illustrates additional components of the inhaler 100, including a main body 105, a medication reservoir 110, a mouthpiece 120, an actuation detector 130, an accelerometer 140, and a processor 150. The main body 105 may be formed of a desirable material, such as plastic, which is lightweight, inexpensive, and easy to mold into any desirable size and/or shape. The medication reservoir 110 may be configured to receive and securely hold the medication canister 50 therein. A valve stem 51 of the medication canister 50 may fit securely in a lower recess of the medication reservoir 110 for channeling any released medication toward the mouthpiece 120. In addition, the valve stem 51 may serve as at least part of the release valve used to expel the medication 55. By pressing the medication canister 50 further into the medication reservoir 110, the valve stem 51 gets pushed into the medication canister 50 and releases the medication 55. The medication 55 released may pass through the valve stem 51 leading from inside the medication canister 50 to an internal conduit 122 of the inhaler 100 that leads to a mouthpiece aperture 124. In this way, the medication canister 50 serves as an actuator configured to trigger a release of the medication 55 from the medication reservoir 110 holding the medication canister 50 to expel through the mouthpiece aperture 124. Alternatively, the medication reservoir 110 may be an enclosed chamber for holding the medication 55 directly therein, which may require additional elements, such as a release valve and an actuator. Thus, the medication canister 50, the medication reservoir 110, and the valve stem 51 may form at least part of a medication release mechanism. As used herein, the term "medication release mechanism" refers to one or more elements of the inhaler that are configured to function alone or in combination to release medication.

The actuation detector 130 may be configured to provide an actuation signal in response to release of the medication from the inhaler. The actuation detector 130 may be a switch or sensor configured to detect activation of the medication release mechanism, which may be associated with a user attempting to dispense medication. For example, the actuation detector 130 may be a sensor configured to detect when a portion of the medication canister 50 contacts a bottom or particular portion of the side of the medication reservoir 110. Such contact may be associated with activation of the medication release mechanism and trigger the actuation detector 130 to provide the processor 150 with an actuation signal associated with the a user trying to dispense the medication 55. Alternatively, the actuation detector 130 may register movement between the medication canister 50 and the medication reservoir 110, which movement may be associated with activation of the medication release mechanism.

The actuation signal provided by the actuation detector 130 may continue for the entire duration of activation, or otherwise provide an activation duration associated with a total period in which the medication release mechanism is activated. For example, the actuation signal may provide the activation duration through one or more signals marking at least the beginning and the end of a continuous period associated with activation of the medication release mechanism. The one or more signals may include one continuous signal lasting as long as the medication release mechanism remains activated, periodic signals while the medication release mechanism remains activated, a pair of signals marking the beginning and end of when the medication release mechanism is activated, or some other indication that may enable the processor 15 to determine the activation duration. The activation duration may be used by the processor 150 to provide timing usage metrics that may be used for determining a quality of use of the inhaler 100.

The accelerometer 140 may be a small micro electromechanical system (MEMS), such as one configured to detect multi-axis movements. In addition, consideration may be given to ensure the accelerometer 140 couples and communicates effectively with the processor 150. For example, the accelerometer 140 may connect to the processor 150 with a multi-master, multi-slave, single-ended, serial computer bus (e.g., I2C) or a Serial Peripheral Interface (SPI) bus. The accelerometer 140 may be used to determine an orientation angle and/or movement (i.e., direction/speed/acceleration) of the inhaler 100. The orientation angle may be used to determine whether and when the inhaler 100 is being held outside the range of preferred orientation angles predetermined to be proper for dispensing the medication 55. In this way, the orientation angle may be used to determine when the inhaler deviates from a preferred orientation by an amount that exceeds the predetermined proper orientation threshold.

The processor 150 may be coupled to the actuation detector 130 and the accelerometer 140. In addition, the processor 150 may be configured to recognize the actuation signal from the actuation detector 130 as a release of the medication 55 from the medication reservoir 110 or at least a user's desire to release (i.e., dispense) the medication 55. In this way, the actuation detector 130 may output an electronic signal (e.g., a voltage) in response to detecting activation of the medication release mechanism, which the processor 150 may recognize as an actuation signal (i.e., a signal informing the processor when the medication release mechanism is being or has been activated). The processor 150 may be configured to recognize measurements or signals received from the accelerometer 140.

Using data from the actuation signal from the actuation detector 130 and measurements from the accelerometer 140, the processor 150 may determine whether the inhaler was activated for an improper usage duration. A determination of an improper usage duration may be based on detecting that the measured orientation of the inhaler exceeds a predetermined proper orientation threshold at some time while medication was being dispensed. An improper usage duration may also reflect that the medication 55 was not dispensed or may have been improperly dispensed during all or part of the activation duration. Thus, a quality of use of the inhaler may be determined by applying a discount of an improper usage duration to the activation duration. A difference between the activation duration and the improper usage duration may represent a period of proper usage of the inhaler 100, which reflects a quality of use of the inhaler. The improper usage duration may provide additional timing usage metrics.

The processor 150 may be any programmable microprocessor, microcomputer or multiple processor chip or chips that may be configured by software instructions (applications) to perform a variety of functions, including the functions of the various aspects described herein. The inhaler 100 may include multiple processors, such as one processor dedicated to wireless communication functions and one processor dedicated to controlling an internal circuit or running other applications. Typically, software applications may be stored in an internal memory 155 before they are accessed and loaded into the processor 150. The internal memory 155 may be sufficient to store the application software instructions. In many devices, the internal memory 155 may be a volatile or nonvolatile memory, such as flash memory, or a mixture of both. For the purposes of this description, a general reference to memory refers to memory accessible by the processor 150 including internal memory 155 or removable memory plugged into the inhaler 100 and memory within the processor 150.

The inhaler 100 may include additional components, such as an onboard battery 160. The onboard battery 160 may power other components, such as the actuation detector 130, the accelerometer 140, and the processor 150. The onboard battery 160 may be a replaceable component.

The inhaler 100 may include a wireless signal transmitter 170, which may be coupled to the processor 150 and configured to transmit data 70 (e.g., an activation signal, orientation angle, movement direction/speed/acceleration, etc.) to a remote computing device (i.e., 400 in FIG. 1A) separate from the inhaler. The data 70 may include the activation signal, the measured orientation of the main body at the time that medication was dispensed, as well as improper usage duration information and any quality of use information, if applicable. In this way, the processor 150 may store a time-of-day associated with each activation signal indicating when medication is dispensed and/or attempted to be dispensed. In addition, a count of a plurality of activation signals may be maintained, each in response to activation of the medication release mechanism. The time-of-day and count may be used for verifying adherence to schedules and proper dosing. Tracking doses and the timing of such doses may be useful to the user and/or medical practitioners. The wireless signal transmitter 170 may include an antenna for transmitting the data 70 as well as any other information collected. In addition, the wireless signal transmitter 170 may include a receiver for receiving signals from a remote computing device. The wireless signal transmitter 170 may establish wireless connections, e.g., Bluetooth®, BLE, or Wi-Fi connections, with remote devices, such as the computing device (see 400 FIG. 1A), and may exchange data with the remote devices.

In an embodiment, the inhaler 100 may alternatively include an inhibitor 145 configured to prevent the inhaler 100 from dispensing the medication 55. The inhibitor 145 may be a restrictive mechanical device that prevents or interrupts the release of the medication 55 from the medication canister 50. As a mechanical device, the inhibitor 145 may block the medication canister 50 from being pressed into the medication reservoir 110, thus preventing the medication 55 from dispensing. The processor 150 may be configured with processor-executable instructions to perform operations further comprising activating the inhibitor 145 in response to the measured orientation of the main body 105 exceeding the predetermined proper orientation threshold. In addition, in response to the processor 150 receiving acceleration data indicating that an acceleration of the inhaler 100 has exceeded a predetermined acceleration threshold, the inhibitor 145 may be activated.

Additional usage metrics may be compiled and used to reflect the quantity and/or quality of use of the inhaler, such as a number of activations of the medication release mechanism, a number of doses remaining, a time of the last activation, a duration/orientation of the last activation, an average duration/orientation of activations, a number of improperly oriented activations, a number of failed attempts to dispense medication, and/or a number of times an inhibitor is activated. Such usage metrics may be transmitted from the inhaler to provide users and/or medical practitioners with valuable information for improving the usage of the inhaler and/or associated activities.

FIG. 2 is a component block diagram illustrating components of the inhaler 100 according to various embodiments. As described above, the inhaler 100 may include a medication reservoir 202 that works in conjunction with a medication canister 204 to generate an aerosol spray of a medication contained in a pressurized state in the medication canister 204. The medication reservoir 202 may selectively release aerosolized medication from the medication canister 204 into a nozzle 206 when activated by a user. In various embodiments, the user input activation may involve manually compressing the medication canister 204 to actuate a button and/or manually pressing a button on or around the medication canister 204. Such user input activation may be detected by an actuation detector 212, which may include a sensing device or circuit, the form and configuration of which depends on the particular type of user input.

In use, a user may inhale mist expelled from the nozzle 206 through an external opening 232 of a mouthpiece 219, causing the aerosolized medication to mix with ambient airflow in area 216, and to be expelled through the external opening 232. In various embodiments, the medication delivery flow from beginning to end (i.e., from the medication canister 204 through the external opening 232) is represented by the flow pathway 218. In various embodiments, the components of the inhaler 100 may be encased in a main body (i.e., a housing) as illustrated in FIGS. 1B and 1C. The mouthpiece 219 may be a ventilator tube.

In various embodiments the inhaler 100 may include a circuit board 222 on which are positioned a processor 210 that is coupled to a communication module 228 (e.g., an RF resource), such as a BLE transceiver, the actuation detector 212, and at least one accelerometer 208. The accelerometer 208 may be configured to sense instantaneous acceleration forces due to gravity on each of the accelerometer's axis. The accelerometer 208 may also sense movements of the inhaler 100 and provide signals indicative of measured accelerations to the processor 210. In an embodiment, the accelerometer 208 may be a three-axis accelerometer that is configured to sense accelerations (including the force of gravity) along three perpendicular axes. The processor 210 may be configured to use signals received from the accelerometer 208 to perform the operations of the embodiment methods described below.

The processor 210 may be configured to stay in a low-power state until the accelerometer 208 detects movement of the inhaler exceeding a predetermined acceleration threshold. In response to determining that the predetermined acceleration threshold is exceeded, the processor 210 may begin sampling the acceleration measurements from the accelerometer 208 periodically to determine an inhaler orientation state. Acceleration measurements may also be used to infer contextual information related to the activity of the user based on movement of the inhaler 100. In the case of pedometer-style movement detection, the processor 210 may relate periodic acceleration events as representative of certain activities, such as walking, jogging, running, or other exercises. If the acceleration events correspond to vigorous shaking or agitation activity, the processor 210 may log the event, recording the duration of shaking and/or the agitation level for the inhaler 100 and medication (e.g., 55 in FIGS. 1B and 1C) contained therein. In this way, in addition to orientation information, the processor 210 may have collected contextual information that may be included when reporting the inhaler 100 is in use or has been used. Contextual information relating to acceleration events may help medical professional improve the effectiveness of the medication and associated appliance. For example, recorded and/or reported acceleration events may be useful to a medical professional deciding whether to provide dosage changes, lifestyle changes, and/or coaching on proper use of the inhaler 100, as may be appropriate.

In various embodiments, the processor 210 may be configured to transmit raw accelerometer data or processed data (e.g., quality of use determinations) to a computing device (e.g., 400 in FIG. 1A) remote to the inhaler 100 using the communication module 228. In addition, the processor 210 may detect that the inhaler 100 is being used, in response to receiving an activation signal from the actuation detector 212. In response to detecting the inhaler 100 is being used, the processor 210 may power up the accelerometer 208 and initialize it. At appropriate times during the inhaler use, the processor 210 may take one or more readings from the accelerometer and compare these readings to baseline readings that would be produced when the device is held in the optimal orientation angle (e.g., P0 in FIG. 1B). The processor 210 may process the accelerometer readings in a number of ways.

In various embodiments, a communication mode may be triggered automatically on the inhaler 100 based on the availability of new data received from the accelerometer 208. In some embodiments, the communication mode maybe triggered manually through user input, or periodically after a default time interval has passed. In various embodiments, when the communication mode is triggered, the processor 210 may prompt setup of a BLE connection to an external device using the communication module 228. In various embodiments, the communication module 228 may include one or more of a Bluetooth controller, a Bluetooth transceiver, and an antenna (not shown).

Figure 3:
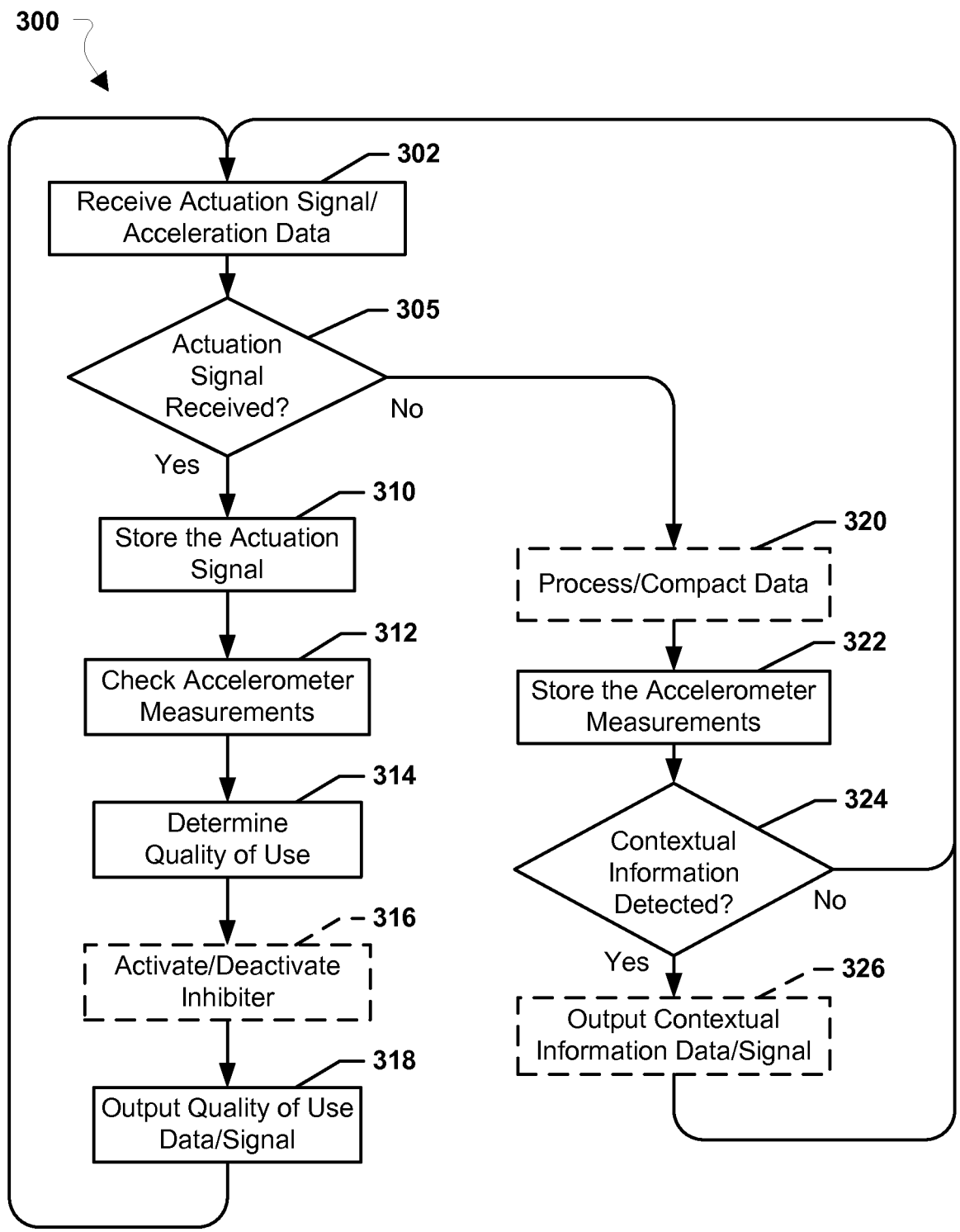
FIG. 3 is a process flow diagram illustrating an aspect method of oral delivery of a medication to a user's lungs with an inhaler according to various embodiments.

FIG. 3 illustrates an embodiment method 300 that may be implemented in an inhaler according to various embodiments. The operations of method 300 may be performed by a processor (e.g., 130 in FIGS. 1B-1C) of an inhaler using data received from an actuation detector (e.g., 130 in FIGS. 1B-1C) and/or an accelerometer (e.g., 140 in FIGS. 1B-1C) as described above.

In block 302, the processor may receive an actuation signal from the actuation detector corresponding to when the canister is depressed to release the medication or may receive acceleration data from the accelerometer. In an embodiment, outputs by the accelerometer may be made in response to the measured accelerations exceeding a reporting threshold value so that only significant accelerations are reported as acceleration data. In a further embodiment, the accelerometer may be configured to remain in a low-power (e.g., sleep) state until accelerations exceed a threshold, in response to which the accelerometer may transition to a powered state to measure accelerations and pass acceleration data to the processor (e.g., if the measured accelerations exceed a reporting threshold). In block 302, the processor may wake from a low-power (i.e., sleep) mode upon receiving the output from the actuation detector and/or accelerometer. In this manner, the processor may conserve power and wake only as needed to respond to or record significant events. Once the processor wakes from the lower power mode or if already awake, in block 302 the processor may receive actuation signals and/or accelerometer data.

In determination block 305, the processor may determine whether an actuation signal is received from the actuation detector. For example, as discussed above, when the canister is depressed to dispense medication, the processor may receive the actuation signal from an actuation detector (e.g., 130 in FIGS. 1B-1C). If only acceleration data is received and no actuation signal is received (i.e., determination block 305="No"), the processor may store accelerometer measurements in block 318 and optionally process/compact data in optional block 316.

In response to receiving the actuation signal (i.e., determination block 305="Yes"), the processor may store the activation signal and newly received acceleration data in a memory in block 310. Receipt of the activation signal may be an indication that the inhaler is in use for dispensing the medication.

In block 312, the processor may check prior accelerometer data and/or the newly received accelerometer data. For example, the processor may access, request, or receive accelerometer measurements, which may measure an orientation of a main body, from an accelerometer (e.g., 140 in FIGS. 1B-1C). The processor may access, request, or receive the accelerometer data from the accelerometer, a memory (e.g., 155 in FIGS. 1B-1C), or other source. The accelerometer data may include a direction and/or speed of movement, which may be used to determine changes in position and/or orientation. In this way, the accelerometer data may be sufficient to determine an orientation of the inhaler and/or whether the inhaler has been agitated a predetermined amount. The predetermined amount may be an amount of agitation needed a properly mixed medication before dispensing.

In block 314, the processor may determine a quality of use of the inhaler based on the actuation signal provided by the actuation detector and the orientation of the inhaler measured by the accelerometer. For example, the quality of use determination in block 314 may include determining whether the accelerometer measurements indicate that the inhaler is oriented such that it exceeds the predetermined proper orientation threshold. Exceeding the predetermined proper orientation threshold during use may be associated with improper usage of the inhaler, since the inhaler may not have dispensed a proper dosage. In contrast, meeting or staying below the predetermined proper orientation threshold may reflect a proper orientation during use. Regardless, the orientation determination may be included in data about the quality of use.

Additionally or alternatively, the quality of use determination in block 314 may include a processor determining whether the inhaler has been agitated a predetermined amount, for example, prior to dispensing (e.g. prior to the actuation signal being received). Insufficient agitation may be associated with improper usage of the inhaler, since the inhaler may not have dispensed a properly mixed medication. Inversely, a level of agitation that meets or exceeds an agitation threshold may reflect a properly mixed dosage. Regardless, the agitation determination may be included in data about the quality of use.

In addition or alternatively, the quality of use determination in block 314 may include a processor determining a proper usage duration. For example, the processor may determine an activation duration based on a total period in which the medication is released. Also, the processor may determine an improper usage duration based on a period during the activation duration in which the orientation of the inhaler deviates from a preferred or acceptable orientation (e.g., an amount that exceeds the predetermined proper orientation threshold). In this way, the processor may discount the activation duration of the inhaler by the improper usage duration for determining the proper usage duration. In this way, the proper usage duration determination may be included in data about the quality of use.

Further, the quality of use determination in block 314 may include determining whether the accelerometer data includes contextual information. For example, movement information contained within the accelerometer data may reflect contextual information if the movement information corresponds to one or more patterns associated with activity performed by a user carrying the inhaler. Patterns of movement or other indicators in accelerometer data may include certain orientations and accelerations of the device that may be associated with a predetermined activity on the part of the user (e.g., walking, jogging, running, or other exercises/activities, or shaking of the inhaler to mix the medication before dispensing). A determination that the user is performing or has performed one or more predetermined activities may be included in data about the quality of use.

Examples of predetermined activities may include vigorous repeated uniform agitation of the inhaler to mix up the medication before it is dispensed or more different levels and/or types of agitation associated activity on the part of the user (e.g., walking, jogging, running, or other exercises). In various embodiments, the processor may analyze accelerometer data to determine whether it matches one or more sets of accelerometer data profiles (i.e., patterns) associated with predetermined activities. Determinations regarding predetermined activities may assess accelerometer data stored in memory for a predetermined window of time just before actuation.

The processor may base determinations regarding contextual information on whether the accelerometer data reflects measurements that meet one or more predetermined acceleration thresholds and recording a number based on the exceeded threshold. Such predetermined acceleration thresholds may be defined to be representative of one or more activities on behalf of the user. For example, a lowest level threshold may reflect no significant activity (e.g., the user/inhaler is still or the user is not holding the inhaler). As another example, a higher level of acceleration may correspond to the user walking, while a higher level may correspond to the user jogging, and an even higher level corresponds to the user running or performing more rigorous activities. Similarly, other types of exercise or activities may be detected in this manner. Alternatively, the processor may process or bundle data into groups of smaller intervals of activity for storage.

Using the accelerometer to monitor movements or accelerations of the inhaler may gather information that may be useful in diagnosing and treating a patient using the inhaler. The accelerometer data may be analyzed by the processor within the inhaler, a computing device held by the user (e.g., a smartphone) or a remote computing device (e.g., a server or a doctor's computer) to correlate and assess patient activity levels against inhaler usage. For example, if the patient's doctor is able to determine from the accelerometer data that asthma episodes (evidenced by activation of the inhaler) may be correlated to a certain activity level, that correlation may be helpful in diagnosing or treating the patient's asthma. As another example, other conditions such as Chronic Obstructive Pulmonary Disease (COPD) require monitoring of the patient's activity level, and an inhaler according to various embodiments carried by the patient may provide such monitoring. More refined monitoring of the patient's activities correlated to inhaler usage may be accomplished by combining acceleration data from the inhaler with other activity measures relating to the user, such as activity indicators from a sensor in the user's smartphone or other wearables (e.g., accelerations, changes in location, phone usage, etc.). Other usage of accelerometer data from the inhaler for patient monitoring and diagnosis are contemplated.

In optional block 316, dispensing of medication may be prevented by activating an inhibitor (e.g., 145 in FIG. 1B). The determination regarding whether or not to activate the inhibitor may be based on the quality of use determination in block 314. For example, in response to the processor determining in block 314 that an orientation of the inhaler exceeds the predetermined proper orientation threshold, the inhibitor may optionally be activated to prevent the inhaler from dispensing medication in optional block 316. Additionally or alternatively, in response to the processor determining that the inhaler has not been agitated a predetermined amount, the inhibitor may be activated in optional block 316. Further, in response to the processor determining that the inhaler is being used properly (e.g., held at a proper orientation), the inhibitor may optionally be deactivated in optional block 316 if it was previously activate, allowing the inhaler to dispense normally. The deactivation of the inhibitor in optional block 316 may not be necessary in various situations, such as when no inhibitor is included, when the inhibitor activation includes an automatic deactivation (i.e., after a predetermined period), or when the inhibitor is not actively preventing the inhaler from dispensing the medication.

In addition or in lieu of preventing dispensing of the medication (i.e., in optional block 316), in block 318, the processor may output quality of use data and/or a signal reflecting the quality of use determination. The output of quality of use data and/or a signal reflecting the quality of use determination may include using a wireless signal transmitter (e.g., 170 in FIGS. 1B-1C) to transmit quality of use data to a computing device remote from the inhaler, such as a mobile communication device, network computer, or other device. In addition, the quality of use data may be stored locally, such as in the onboard memory (e.g., 155 in FIGS. 1B-1C). The output of a quality of use signal may include an indication to the user, such as a local sound and/or visual indication provided on the inhaler (i.e., a beep or an illuminated light or display).

The quality of use data and/or signal may include the determination that the first measured orientation of the main body exceeds or does not exceed the predetermined proper orientation threshold and/or that the inhaler has or has not been agitated a predetermined amount. In addition, the quality of use data and/or signal may also include stored accelerometer data. Accelerometer data may include contextual information, such as certain conditions that may be of significance if the conditions occur prior to use of the inhaler to dispense the medication, such as agitation, or after dispensing medication. Alternatively, the inhaler may conserve power by only outputting accelerometer data in response to either proper or improper use of the inhaler. As a further alternative, the timing of the output of the quality of use data/signal and/or a determination regarding whether to include accelerometer data in the quality of use data may be based on a scheduled time, a cycle for reporting such data, or when the data stored in the memory has reached a threshold amount. In this way, the inhaler may conserve power.

Following, the output of the quality of use data and/or signal in block 318, the process may return to block 302 to receive or await receipt of a further actuation signal and/or acceleration data.

Referring back to determination block 305, if the processor receives acceleration data but no actuation signal (i.e., determination block 305="No"), the processor may optionally process and/or compact accelerometer data into a more compact format representative of the received accelerometer measurement in optional block 320.

In block 322, the processor may store the accelerometer data in a memory (e.g., 155 in FIGS. 1B-1C). As part of the operations in block 322, the processor may store the data in a circular buffer to store only the most recent data within a recording window (e.g., one hour, one day, one week, etc.). In this manner, the processor may work within limits of the available memory, such as only storing a certain number of days, hours, or minutes of data.

In determination block 324, the processor may determine whether the accelerometer data includes contextual information, as described above with regard to block 314. In response to determining that contextual information is detected from the accelerometer measurements (i.e., determination block 324="Yes"), the processor may optionally output the contextual information and/or a signal reflecting the contextual information in optional block 326. The output of contextual information data and/or a signal reflecting the contextual information may include using a wireless signal transmitter (e.g., 170 in FIGS. 1B-1C) to transmit contextual information data to a computing device remote from the inhaler, such as a mobile communication device, network computer, or other device. In addition, the contextual information data may be stored locally, such as in the onboard memory (e.g., 155 in FIGS. 1B-1C). The output of a contextual information signal may include an indication to the user, such as a local sound and/or visual indication provided on the inhaler (i.e., a beep or an illuminated light or display).

Alternatively, the timing of the output of the contextual information data/signal and/or a determination regarding whether to output the contextual information data/signal may be based on a scheduled time, a cycle for reporting such data, or when the data stored in the memory has reached a threshold amount. In this way, the inhaler may conserve power. For example, the inhaler may only output the contextual information data/signal in response to activation of the inhaler.

If the processor does not detect predetermined events from the accelerometer measurements (i.e., determination block 324="No"), the processor may return to block 302 to receive or await the receipt of an actuation signal and/or further acceleration data. Similarly, in response to detecting contextual information (i.e., determination block 324="Yes"), whether or not the contextual information data/signal is output in optional block 326, the processor may return to block 302 to receive or await the receipt of an actuation signal and/or further acceleration data.

Figure 4:
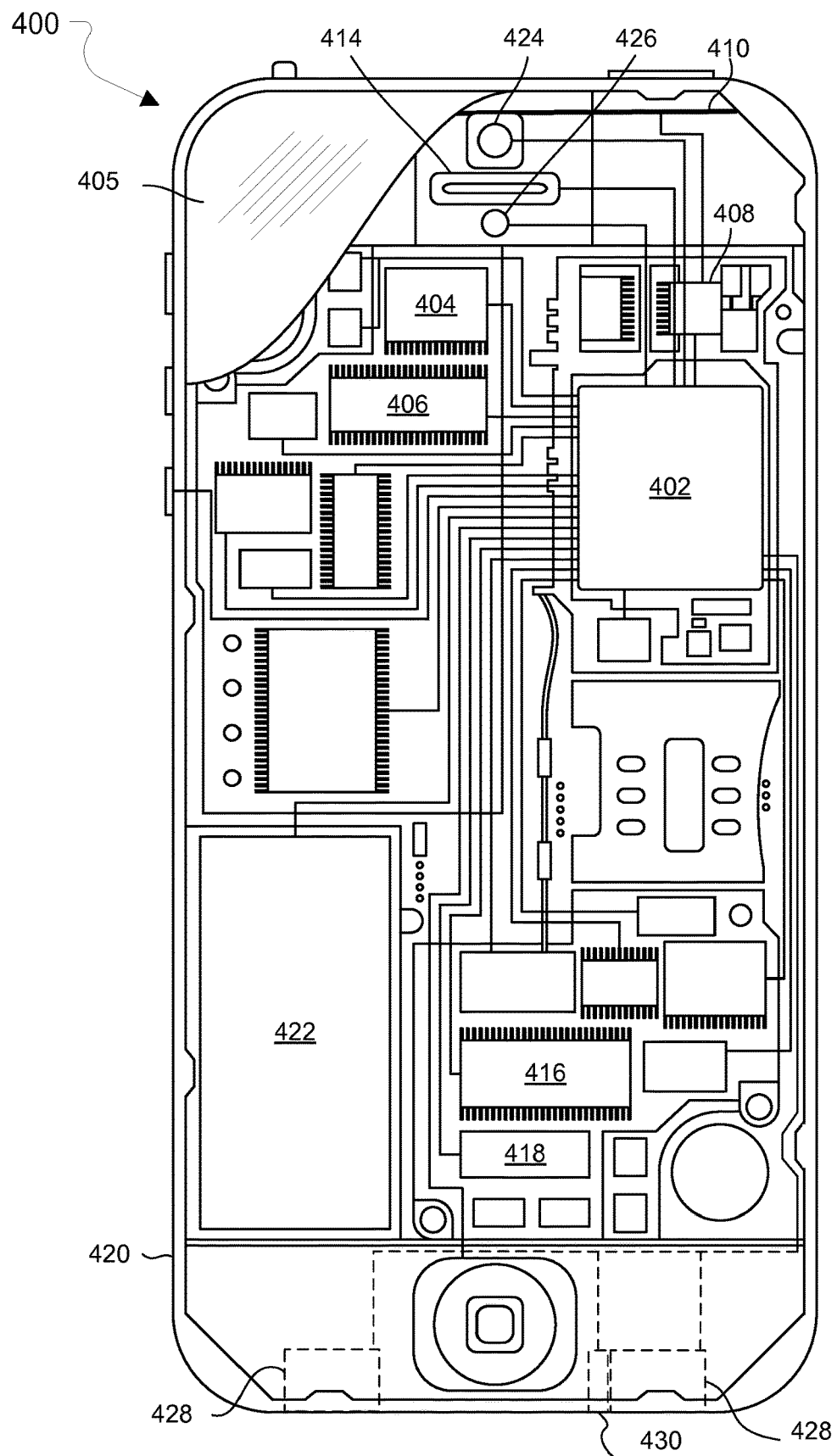
FIG. 4 is a component block diagram of a computing device suitable for use with the various embodiments.

The data from an inhaler device according to the various embodiments may be communicated to a variety of external computing devices for processing, display, and relaying to other systems and computers. An example of such an external computing device 400 suitable for use in various embodiments in the form of a smart phone is illustrated in FIG. 4. The computing device 400 may exchange data from the inhaler (e.g., 100) discussed above, and may perform one or more of the operations of the method 300 described above. For example, a dispensing signal including the correlation of the measured orientation of the main body to the detected release of the medication may be sent from the inhaler 100 to the computing device 400.

In various embodiments, the computing device 400 may include a processor 401 coupled to a touch screen controller 404 and an internal memory 402. The processor 401 may be one or more multicore ICs designated for general or specific processing tasks. The internal memory 402 may be volatile or non-volatile memory, and may be secure and/or encrypted memory, or unsecure and/or unencrypted memory, or any combination thereof. The touch screen controller 404 and the processor 401 may also be coupled to the display 405, which may be a touch screen panel, such as a resistive-sensing touch screen, capacitive-sensing touch screen, infrared sensing touch screen, etc. The computing device 400 may have one or more radio signal transceivers 408 (e.g., Peanut®, Bluetooth®, BLE, Zigbee®, Wi-Fi, RF, cellular, etc.) and antennae 410, for sending and receiving, coupled to each other and/or to the processor 401. The radio signal transceivers 408 and antennae 410 may be used with the above-mentioned circuitry to implement the various wireless transmission protocol stacks and interfaces. The computing device 400 may include a cellular network wireless modem chip 416 that enables communication via a cellular network, and may be coupled to the processor. The computing device 400 may include a peripheral device connection interface 418 coupled to the processor 401. The peripheral device connection interface 418 may be singularly configured to accept one type of connection, or multiply configured to accept various types of physical and communication connections, common or proprietary, such as USB, FireWire, Thunderbolt, or PCIe. The peripheral device connection interface 418 may also be coupled to a similarly configured peripheral device connection port (not shown). The computing device 400 may also include speakers 414 for providing audio outputs. The computing device 400 may also include a housing 420, constructed of a plastic, metal, or a combination of materials, for containing all or some of the components discussed herein. The computing device 400 may include a power source 422 coupled to the processor 401, such as a disposable or rechargeable battery. The rechargeable battery may also be coupled to the peripheral device connection port to receive a charging current from a source external to the computing device 400.

Processors of computing devices suitable for use in various embodiments may be any programmable microprocessor, microcomputer or multiple processor chip or chips that can be configured by software instructions (applications) to perform a variety of functions, including the functions of the various embodiments described above. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store the application software instructions. In many devices, the internal memory may be a volatile or nonvolatile memory, such as flash memory, or a mixture of both. For the purposes of this description, a general reference to memory refers to memory accessible by the processors including internal memory or removable memory plugged into the various devices and memory within the processors.

Further, those of skill in the art will appreciate that the foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. An inhaler for oral delivery of medication, the inhaler comprising:
    an actuation detector configured to provide an actuation signal in response to release of the medication from the inhaler;
    an accelerometer configured to measure an orientation angle of the inhaler;
    a processor coupled to the actuation detector and the accelerometer, wherein the processor is configured with processor-executable instructions to perform operations to:
        determine whether the orientation angle of the inhaler measured by the accelerometer departs from a preferred orientation angle by an amount that exceeds a predetermined proper orientation threshold; and
        determine a quality of use of the inhaler based on the actuation signal provided by the actuation detector and the orientation of the inhaler measured by the accelerometer, wherein the quality of use comprises an improper orientation angle in response to determining that the orientation angle of the inhaler departs from the preferred orientation angle by the amount that exceeds the predetermined proper orientation threshold;
    an inhibiter configured to prevent the inhaler from dispensing the medication, wherein the inhibiter is a restrictive mechanical device that prevents the release of the medication from the inhaler, and wherein the processor is further configured with processor-executable instructions to activate the inhibiter based on the quality of use of the inhaler reflecting the improper orientation angle; and
    an indicator configured to alert a user regarding the quality of use, wherein the alert comprises information about the determined improper orientation angle.

2. The inhaler of claim 1, wherein the processor is further configured with processor-executable instructions to:
    receive from the accelerometer an accelerometer measurement indicating movement information of the inhaler; and
    determine whether the movement information is contextual information associated with activity performed by a user carrying the inhaler.

3. The inhaler of claim 2, wherein the contextual information includes a predetermined type of activity by the user.

4. The inhaler of claim 1, wherein the processor is further configured with processor-executable instructions to perform operations to:
    determine an activation duration based on a total period in which the medication is released; and
    determine an improper usage duration, wherein the improper usage duration is a period during the activation duration in which the orientation angle of the inhaler deviates from the preferred orientation angle by an amount that exceeds a predetermined proper orientation threshold, wherein determining the quality of use of the inhaler includes discounting the activation duration by the improper usage duration.

5. The inhaler of claim 1, wherein the processor is further configured with processor-executable instructions to perform operations to:
    determine whether the inhaler has been agitated a predetermined amount, wherein the quality of use reflects an improper agitation in response to determining that the inhaler has not been agitated the predetermined amount before the medication is released.

6. The inhaler of claim 1, further comprising:
    a wireless signal transmitter coupled to the processor, wherein the wireless signal transmitter is configured to transmit data to a computing device remote from the inhaler to enable the computing device to determine the quality of use of the inhaler.

7. The inhaler of claim 1, further comprising:
    a memory coupled to the processor and configured to store data indicating the quality of use of the inhaler.

8. The method of claim 1, wherein the processor is further configured with processor-executable instructions to activate the indicator based on the quality of use of the inhaler determined.

* * * * *